US012765750B2

(12) United States Patent
Busch et al.

(10) Patent No.: US 12,765,750 B2
(45) Date of Patent: Oct. 20, 2026

(54) ENDOSCOPE WITH CONNECTOR

(71) Applicant: AMBU A/S, Ballerup (DK)

(72) Inventors: David Busch, Weyarn (DE); Günter Wilhelm Schütz, Augsburg (DE); Martin Johst Christensen, Copenhagen Ø (DK)

(73) Assignee: AMBU A/S, Ballerup (DK)

( * ) Notice: Subject to any disclaimer, the term of this patent is extended or adjusted under 35 U.S.C. 154(b) by 527 days.

(21) Appl. No.: 18/266,972

(22) PCT Filed: Dec. 8, 2021

(86) PCT No.: PCT/EP2021/084831
§ 371 (c)(1),
(2) Date: Jun. 13, 2023

(87) PCT Pub. No.: WO2022/128689
PCT Pub. Date: Jun. 23, 2022

(65) Prior Publication Data

US 2024/0057851 A1 Feb. 22, 2024

(30) Foreign Application Priority Data

Dec. 14, 2020 (DE) ..................... 10 2020 133 405.2

(51) Int. Cl.
*A61B 1/00* (2006.01)
*A61B 1/01* (2006.01)
*A61B 1/018* (2006.01)

(52) U.S. Cl.
CPC ............ *A61B 1/00128* (2013.01); *A61B 1/01* (2013.01); *A61B 1/018* (2013.01)

(58) Field of Classification Search
CPC ....... A61B 1/00128; A61B 1/01; A61B 1/018; A61B 1/0011; A61B 1/00137;
(Continued)

(56) References Cited

U.S. PATENT DOCUMENTS 4,972,828 A 11/1990 Ito
5,868,665 A 2/1999 Biggs
(Continued)

FOREIGN PATENT DOCUMENTS

CN 104274147 B 1/2016
EP 1002553 A1 5/2000
(Continued)

OTHER PUBLICATIONS

German Search Report received for DE Application No. 102020133405.2, mailed on Sep. 20, 2021, 12 pages (6 pages of English Translation and 6 pages of Original Document).
(Continued)

*Primary Examiner* — Anh Tuan T Nguyen
*Assistant Examiner* — Li-Ting Song
(74) *Attorney, Agent, or Firm* — Faegre Drinker Biddle & Reath LLP

(57) ABSTRACT

An endoscope, a method to make the endoscope, and a system including the endoscope and a monitor. The endoscope includes a distal tip; a handle; an insertion tube and a bending section, the insertion tube and the bending section connecting the handle and the distal tip; a working channel provided in the insertion tube and the bending section and extending from the handle towards the distal tip; a first part and a second part, the first part attachable to the second part to form a connector having a first channel with a first inlet opening, a second channel with a second inlet opening, the first channel joining with the second channel form a joint channel having an outlet opening to connect the first inlet opening and the second inlet opening with the outlet opening, the outlet opening in connection with the working channel.

17 Claims, 7 Drawing Sheets

(58) Field of Classification Search
CPC ............ A61B 1/00119; A61B 1/00066; A61B 1/0052; A61B 1/015
See application file for complete search history.

(56) References Cited

U.S. PATENT DOCUMENTS

| | | | | |
|---|---|---|---|---|
| 5,888,191 | A | 3/1999 | Akiba et al. | |
| 7,335,182 | B1 | 2/2008 | Hilaire | |
| 7,922,650 | B2 | 4/2011 | McWeeney et al. | |
| 10,321,804 | B2 | 6/2019 | Jacobsen et al. | |
| 2004/0193011 | A1* | 9/2004 | Akiba | A61B 1/0052 600/122 |
| 2007/0238928 | A1* | 10/2007 | Maseda | A61B 1/00137 600/153 |
| 2014/0066706 | A1 | 3/2014 | McWeeney et al. | |
| 2015/0374214 | A1* | 12/2015 | Fan | A61B 1/00128 600/104 |
| 2016/0249792 | A1 | 9/2016 | Ogawa | |
| 2016/0338577 | A1 | 11/2016 | Viebach et al. | |
| 2018/0338672 | A1 | 11/2018 | Krimsky et al. | |
| 2020/0337529 | A1* | 10/2020 | Chu | A61M 25/0028 |
| 2020/0359879 | A1 | 11/2020 | Cahill et al. | |
| 2021/0145258 | A1* | 5/2021 | Takahashi | A61B 1/015 |
| 2021/0235973 | A1 | 8/2021 | Gray et al. | |
| 2021/0338065 | A1 | 11/2021 | Yoshinaga et al. | |
| 2022/0096156 | A1* | 3/2022 | Talbot | A61B 18/14 |
| 2022/0409013 | A1* | 12/2022 | Kambe | A61B 1/00006 |
| 2024/0156334 | A1* | 5/2024 | Nakamura | A61B 1/0057 |

FOREIGN PATENT DOCUMENTS

| | | | |
|---|---|---|---|
| EP | 3415073 | A2 | 12/2018 |
| FR | 2050611 | A5 | 4/1971 |
| GB | 2126018 | * | 3/1984 |
| GB | 2126018 | A | 3/1984 |
| GB | 2463067 | A | 3/2010 |
| WO | 92/22345 | A1 | 12/1992 |
| WO | 97/40739 | A1 | 11/1997 |
| WO | 2010/023460 | A1 | 3/2010 |

OTHER PUBLICATIONS

International Search Report and Written Opinion received for PCT Patent Application No. PCT/EP2021/084831, mailed on Apr. 4, 2022, 10 pages.

* cited by examiner

ENDOSCOPE WITH CONNECTOR

CROSS-REFERENCE TO RELATED APPLICATIONS

This application is a National Phase entry under 35 U.S.C. § 371 of International Application No. PCT/EP2021/084831, filed Dec. 8, 2021, which claims the benefit of and priority from German Patent Application No. DE 10 2020 133 405.2, filed Dec. 14, 2020; said applications are incorporated by reference herein in their entirety.

TECHNICAL FIELD

The present disclosure relates to an endoscope comprising: a handle, a working channel, a connector in the handle, a system comprising the endoscope and a monitor, and a method of making the endoscope. More specifically, the endoscope includes a connector in the handle having two inlets and one outlet connected to the working channel.

BACKGROUND

Endoscopes and similar specialized instruments such as bronchoscopes, arthroscopes, colonoscopes, laparoscopes, gastroscopes and duodenoscopes are well known from the state of the art and are used for visual examination and diagnosis of hollow organs and body cavities, as well as to assist in surgery, e.g. for a targeted tissue sampling. Basically, a distal tip unit of an endoscope, which is connected to an endoscope handle via an insertion tube and a bending section, can be inserted into a hollow organ or body cavity to be investigated with the endoscope. Both reusable and disposable endoscopes are known from the state of the art.

Known endoscopes usually contain (a) steering/control wire(s) that is/are pulled and released to bend a (flexible) bending section of the endoscope, such as a flexible shaft, in order to tilt the distal tip unit. The rotating force being applied to (a) handle wheel(s) provided at the endoscope handle by a user is basically transmitted into a pulling force acting on the steering wire in an axial direction of the steering wire. Thereby, the connection of the steering wire to the handle wheel is essential for transmitting the rotating force from the handle wheel to the steering wire.

In addition, for guiding medical instruments, such as forceps, into the patient's body cavity, a working channel is arranged or formed within the insertion tube and the bending section. In known endoscopes, this working channel is usually implemented/formed as a flexible tube arranged/accommodated/supported in a lumen extending through the insertion tube and the bending section in a longitudinal direction from the endoscope handle to the distal tip unit. Besides the guiding of medical instruments such as biopsy tools to the distal tip unit, usually the working channel is also used for a suction/vacuum function in order to suck fluid and/or tissue from the distal tip unit towards the endoscope handle. A conventional endoscope is disclosed for example in U.S. Pat. No. 10,321,804 B2.

Some endoscopes comprise a connector such as a Y-connector connecting a biopsy channel to the working channel of the endoscope. WO 97/40739 A1 for example discloses a surgical instrument with endoscopic viewing capabilities. Herein, a Y-connector having a luer lock on its proximal end is formed onto the handle of the surgical instrument. It contains a lumen that is in fluid connection with a lumen of a respective tube. However, such Y-connector needs to be formed/moulded in a cost intensive and challenging manner.

In general, endoscopes and its Y-connectors are difficult to produce, since they require a moulding with core parts, in particular with rotational core parts due to its special geometry. Such production comes along with significant costs, since highly expensive tools and several production steps are required in order to create the Y-connector. In addition, a design of the Y-connector is limited by the moulding method. Besides, in a case where a Y-connector is integrally formed directly on the endoscope (handle), a handling of the endoscope with the Y-connector during manufacturing further increases a level of difficulty.

BRIEF DESCRIPTION OF THE DISCLOSURE

The tasks and objectives of the present disclosure are to eliminate or at least to reduce the disadvantages of the prior art. In particular, an endoscope with a connector and a method shall be provided, in which an endoscope, in particular a connector of an endoscope, can be efficiently and cost effectively produced with reduced tooling costs. A further task and objective of the present disclosure is to provide an endoscope with flexible capabilities, in which components such as a connector can even easier be assembled and replaced, thus further simplifying an assembly process of the endoscope. Besides, a design of a connector shall be more freely configurable.

The present disclosure relates to an endoscope, in particular single-use endoscope, comprising: a distal tip unit configured to be inserted into a patient's body cavity; a proximal endoscope handle; an insertion tube and a bending section, the insertion tube and the bending section connecting the endoscope handle and the distal tip unit; and a working channel provided in the insertion tube and the bending section and extending from the endoscope handle towards the distal tip unit.

The endoscope further comprises a connector, preferably a Y-connector, that is adapted to be attachable to the endoscope, especially to the endoscope handle. Herein, the connector comprises a first (fluid) channel/lumen having a first inlet/entrance opening and a first longitudinal axis, in particular a (connector) working channel, and a second (fluid) channel having a second inlet/entrance opening and a second longitudinal axis, in particular a (connector) biopsy channel. The second channel joins with/into the first channel, so that the connector has an outlet opening being in (fluid) connection with the first inlet opening and with the second inlet opening (like a branch). The outlet opening, when attached to the endoscope, is in (fluid) connection with the working channel of the endoscope. Further, the connector is a multi-piece connector comprising at least a first part/piece and a separate second part/piece that are attached/connected/fixed/joined, preferably by gluing or ultrasonic welding, to each other. All parts of the multi-piece-connector together are forming/constituting the connector of the endoscope, so if one part is missing, in particular the fluid channels are not fully formed/provided.

One main idea of the present disclosure is that the endoscope and the connector are adapted to each other so that they can be separately/individually produced and, later on, the connector can be attached to the endoscope, in particular to the endoscope handle. In other words, the connector has such a structure, that it geometrically form fits with a corresponding structure of the endoscope, in particular the endoscope handle, in order to be attachable to the endoscope. By doing so, a modular endoscope is provided having the capability to easily assemble the connector. The connector may further be adapted to be detachable from the endoscope, in particular from the endoscope handle, to enable replacement of the connector as well, or alternatively the connector may be permanently fixed to the endoscope, in particular to the endoscope handle, after assembly by for example a snap connection, glue or ultrasonic welding, e.g. to avoid accidental disassembly. Thereby, the connector can be designed independently and best for its individual production in order to adapt the producing steps for a highly efficient and cost effective production and assembly method.

Building on this idea above, since the connector can be produced individually, a further main idea is to adapt the structure of the connector for its best possible production by not producing a single-piece connector but a multi-piece connector. In this way, the connector can be “divided” into pieces that are designed and produced separately and are attached or fixed together later on. In particular, a level of difficulty of producing, preferably moulding, the pieces of the connector can be split and target-oriented assigned to one or more specific piece(s). In addition, a level of difficulty is lowered in general, since difficult production steps may now be completely omitted.

In other words, the present disclosure provides an endoscope, in which the endoscope and the connector, preferably a Y-Connector, are adapted to each other to be produced separately. During assembly, the connector can be easily attached to the endoscope. With such a configuration of the endoscope, a modular design of the endoscope and the connecter is provided. Further, since the connector is not a single-piece connector but a specifically designed multi-piece connector comprising at least two pieces/parts, in which each piece/part of the connector can be produced separately in an individually adapted efficient manner, tooling costs can significantly be reduced and a degree of freedom of the design of the connector can be increased. Contrary to what could be expected it is found that providing a multi-piece connector instead of a single-piece connector has more advantages than disadvantages in view of production speed, production cost and effectiveness of the connector.

In the present disclosure, “distal” basically means “in a direction away from a user/physician towards a patient” and “proximal” basically means “in a direction towards the user/physician away from the patient”.

In addition, in the present disclosure, a “channel” basically means an inner fluid tight lumen, in which fluid can be transferred from an inlet of the channel to an outlet of the channel.

Further, in the present disclosure, an “opening” basically means a geometric opening having an (circumferential) outline that serves as an access port to the respective channel.

Advantageous embodiments are claimed in the dependent claims and/or are explained below.

Preferably, the connector is (in a configuration of) a two-piece connector consisting of only the first part and the second part. Thereby, a number of pieces and its respective productions is reduced to a minimum and assembly is eased.

According to one aspect of the disclosure, the first part and/or the second part has such a structure that it is mouldable without a core mould piece. By dividing the connector into specific portions/parts of the connector that are later assembled together, at least one part of the connector can be configured such that it has a simple structure that allows a moulding without any core mould pieces. In particular, one part may have a structure with no undercuts in one direction, thereby enabling this part of the connector to be produced via injection moulding for example. In other words, the first part and/or the second part may be produced by a moulding process that does not use any core mould pieces.

According to another aspect of the disclosure, the first part and/or the second part can have such a structure that it is mouldable with only core mould pieces but without rotational core mould pieces. In particular, the first part and/or the second part may be produced by a moulding method using (only) core mould pieces. Such structure is more complex than a structure that is mouldable without any core mould pieces, but still provides an effective and cost reduced way to produce a respective part of the connector. In particular, the respective part may comprise a segment of the channel along its longitudinal axis that is forming the respective opening and using a core for moulding this part of the channel.

According to another preferred embodiment, the first part and the second part may be attached and glued together along a partition line, thereby sealing the first channel and the second channel of the connector. By doing so, a fluid tight first channel and fluid tight second channel can easily and securely be obtained. In addition, by gluing the (at least two) parts of the connector with each other (material bonding) along the partition line, a cost effective assembly and manufacturing can be performed. Preferably, the partition line to be glued is distant to the channel or, in other words, between the channel and the partition line, a border wall or an elongated projection is provided in order to geometrically separate the channel from the gluing area.

According to another aspect of the disclosure, the first part and/or the second part may comprise at least one balcony in form of a protrusion or a bar at least partially extending along the partition line, the balcony serving as an extended platform for supporting an assembly and a glue to flow into a gap between the first part and the second part. Preferably, the first part and/or the second part may comprise at its contact areas (partition lines) additional bar stripes as the balconies that extend besides the contact areas and enlarge a support surface, especially for gluing the second part to the first part. The balcony further facilitates an assembly in that a glue pen can rest on the balcony and glue may flow into the gap between the first part and the second part, especially due to a capillary effect. Preferably, the balcony has a surface that continuously transitions from respective predetermined contact areas (where the first part stands in contact with the second part), in particular is plane and lies on the same plane as the (local) respective contact area.

It is advantageous, when the first part of the connector comprises a first adapter portion/segment forming the first inlet opening of the first channel and/or comprises a second adapter portion forming the second inlet opening of the second channel and/or comprises an outlet adapter portion forming the outlet opening. The respective adapter portions are adapted to be attachably coupled to and preferably detachably coupled from a respective connecting/coupling portion of the endoscope, preferably of the endoscope handle, and form the circumferentially closed access port to the respective channel. Preferably, the respective adapter portions of the connector may be permanently fixed to the respective coupling portions of the endoscope after assembly by a snap connection and/or glue and/or ultrasonic welding in order to avoid accidental disassembly.

It is particularly advantageous, when the first part of the connector comprises the first adapter portion and the second adapter portion and the outlet adapter portion as well as a bottom half central portion (between the adapter portions) that interconnects the adapter portions with each other. In addition, the second part may be a corresponding top half central portion in the form of a central cover that is a counterpart to the bottom half central portion and is adapted to cover the bottom half central portion, thereby forming the first and second channels. By doing so, the top half central portion can have such a structure that it is easily mouldable without any core mould pieces, whereas the first part having all the adapter portions has such a structure that it can be moulded with core mould pieces but since the central portion is divided in the bottom half central portion and the top half central portion, it can be moulded without any rotational core mould pieces. Preferably, a junction section/segment where the second channel joins with/into the first channel is formed in the bottom half central portion and in the corresponding top half central portion. Thereby, the top half central portion is adapted to cover the junction section.

Preferably, the bottom half central portion and the second part as the top half central portion have essentially a same basic shape of half shells that are axially symmetric to a cutting plane that is spanned by the first longitudinal axis of the first channel and the second longitudinal axis of the second channel, each half shell comprising a semi-cylinder-shaped segment along the first longitudinal axis for the first channel and along the second longitudinal axis for the second channel, the cylinder-shaped segments merging into each other where the channels join each other.

According to a preferred embodiment, the first adapter portion and/or the second adapter portion and/or the outlet adapter portion comprises at its side facing away from its respective opening on its radial outer surface a partly circumferential, preferably semi-circular, groove that extends perpendicular to (partly around) the longitudinal axis of the respective adapter portion respectively to the channel of the adapter portion, for form-fitting and (at least partly) sealing with another part of the connector. In particular, the first adapter portion and/or the second adapter portion and/or the outlet adapter portion comprises at its side facing away from the respective opening a first partly-circular, preferably semi-circular, arch having a first radial outer diameter and an adjacent/directly following second partly-circular, preferably semi-circular, arch having a second radial outer diameter. Herein, the adjacent arches are aligned coaxial to each other and to the (local) longitudinal axis of the respective adapter. The second radial outer diameter of the second partly-circular arch that is further away from the respective opening is larger than the first radial outer diameter, thereby forming an partly-circular, preferably semi-circular, groove and an adjacent partly-circular, preferably semi-circular, ring projection for form-fitting with a corresponding partly-circular, preferably semi-circular radial inner projection and an adjacent radial inner partly-circular, preferably semi-circular, ring-groove formed in the corresponding other part of the connector.

According to another preferred embodiment, the first adapter portion may comprise a first sleeve and an adjacent/directly following coaxial second sleeve, the first sleeve forming the inlet opening having a first inner diameter and the second sleeve having a second inner diameter that is smaller than the first inner diameter, thereby forming a radial stop step in the axial direction. In this way, a docking structure for a tubular coupling portion of the endoscope is provided. If a tubular coupling portion of the endoscope is inserted inside the first sleeve and pushed further toward a central portion of the connector, this tubular coupling portion abuts against the ring shaped stop of the first adapter portion and a position of the endoscope and the connector relative to each other is predetermined (limited). Such structure of the first adapter portion is mouldable with a core mould piece but without any need of rotational core mould pieces.

In particular, the second adapter portion of the second channel may be in the form of a sleeve having a coaxial ring-shaped flange at its radial outer surface at its free end/at its end side/at the axial position of the second inlet opening. Preferably, the second adapter portion may further comprise two wings on opposite outer sides of the sleeve, each wing being in the form of a flat plate extending from the radial outer sleeve surface in the radial outward direction and in the axial direction of the sleeve, for improved manual handling, form fitting with and/or alignment within the endoscope. Such a structure of the second adapter portion is in particular mouldable with a core mould piece but without any need of rotational core mould pieces.

It is further preferred, when the outlet adapter portion may be in the form of a sleeve having a coaxial ring-shaped flange at its radial outer surface distant to the outlet opening, the flange preferably being arranged to abut against the attached second part. This flange is kind of a washer/shim that is aligned coaxial to the longitudinal axis of the outlet adapter portion at its rear end serving as a separation structure between a second part (as a central portion of the connector) and a front side coupling portion of the endoscope that may be plugged onto the sleeve of the outlet adapter portion. Such a structure of the outlet adapter portion is in particular mouldable with a core mould piece but without any need of rotational core mould pieces.

According to another aspect of the present disclosure, the first inlet opening, the second inlet opening and the outlet opening are in/have a circular shape. Preferably, the first adapter portion and/or the second adapter portion and/or the outlet adapter portion may have a tubular inner lumen. The first inlet opening may be (aligned) coaxial to the outlet opening forming a straight longitudinal axis throughout the first channel. The second inlet opening may have a local longitudinal axis (a second opening-axis) that intersect the straight longitudinal axis of the first channel with an angle, in particular with an angle between 30° and 50°, especially preferred with an angle of 40° for a simple and easy introduction of a medical tool.

It is also conceivable, when the second channel, starting from the second inlet, has a channel portion with a straight section of the longitudinal (central) axis/midline and a subsequent/following channel portion with a curved section of the longitudinal axis that lead into/to the longitudinal axis of the first channel. Thereby a favourable merge/joining of the first channel and the second channel is achieved. Preferably a central bar between the first channel and the second channel is in the form of a tapered, V-shaped wedge similar to a wedge plow, the first channel joining the second channel at the tip of the wedge.

According to another aspect of the disclosure, the connector can comprise, preferably consist, of plastic as material. Preferably, the material of the connector or at least one part of the connector may be a thermoplast and/or a thermosetting polymer that is easy to mould.

Preferably, the connector is a biopsy connector that is adapted to/for a biopsy tool, which may be inserted through the second opening and may be advancing to the working channel to the distal tip unit in order to manipulate a tissue in the area of the tip unit.

In addition, the present disclosure relates to a method for producing an endoscope having a multi-piece connector, preferably an endoscope as described above. The method comprises the steps of producing, preferably moulding, a first part of the multi-piece connector; producing, preferably moulding, a second part of the multi-piece connector; attaching the second part of the multi-piece connector to the first part of the multi-piece connector and assembling the multi-piece connector; and attaching the multi-piece connector to the endoscope, preferably permanently attaching to the endoscope by gluing and/or ultrasonic welding. With such method, the first part and the second part are moulded individually and later on are attached to each other and subsequently to the endoscope. This method comes along with increased production speed, reduced production cost and better effectiveness of the production of the connector and thus the endoscope. In particular, the method reduces tooling costs.

According to another aspect of the disclosure, the step of moulding the first part of the multi-piece connector may further comprise the (sub)steps: arranging at least a first straight, preferably cylindrical or tubular, moulding core/core mould piece in a moulding device, preferably an injection moulding device; moulding, preferably injection moulding, the first part of the connector, wherein during moulding, the first straight moulding core serves to form an adapter portion of the connector, the adapter portion having an opening; and removing the first straight moulding core by a translational movement. In particular, the moulding of the first part is done without rotational core mould pieces. In the present disclosure, "straight" basically means that the moulding core has a straight central axis along which it extends. Preferably, a size/an extension of the straight core mould piece in a direction perpendicular to the central axis decreases along the central axis. Due to the shape of a straight moulding core, the moulding core can be removed by a translational movement after moulding, especially in the direction of its straight central axis.

According to a preferred embodiment of the method, the step of producing the first part of the multi-piece connector may comprise the steps: in addition of arranging the first straight moulding core, arranging a second straight moulding core and arranging a third straight moulding core in the moulding device; in the step of moulding the first part of the connector, the first straight moulding core serves/is used to form a first adapter portion with a first inlet opening of a first channel of the connector, the second straight moulding core serves to form a second adapter portion with a second inlet opening of a second channel of the connector and the third straight moulding core serves to form an outlet adapter portion with an outlet opening of the connector; and in addition of removing the first straight moulding core, removing the second straight moulding core and removing the third straight moulding core each by a translational movement. With such a method, the first part with three adapter portions is moulded using three core mould pieces but no rotational core mould pieces.

According to yet another preferred embodiment, the step of attaching the second part to the first part of the multi-piece connector further comprises gluing the two parts together, preferably gluing along a partition line, thereby permanently fixing, and preferably sealing, the first part to the second part.

Preferably, the step of moulding the second part of the multi-piece connector comprises the step of injection moulding the second part in an injection moulding device, in particular injection moulding without a core mould piece.

To sum up, the present disclosure relates to an endoscope comprising a connector that in particular connects a biopsy channel to a working channel. The connector, preferably a Y-connector, is configured as a multi-part component, especially a two-part component ("two-part piece"), thereby enabling to be moulded in multiple pieces. Preferably, the connector is moulded in two pieces, a bottom part (first part) and a top part (second part). The top part may be (a simple structure and thus) simple to mould without any core mould pieces. The bottom part may be a more complex structure and may require some core mould pieces but no rotational core mould pieces. In particular, the top part and the bottom part are attached and sealed by gluing along a partition line. Such a connector respectively such an endoscope has the advantage of reduced tooling costs. The connector, in particular a biopsy Y-connector, is preferably attached to a handle of the endoscope.

BRIEF DESCRIPTION OF FIGURES

The disclosure is explained in more detail below using preferred embodiments and referring to the accompanying figures.

The figures are schematic in nature and serve only to understand the disclosure. Identical elements are marked with the same reference signs. The features of the different embodiments can be interchanged among each other.

DETAILED DESCRIPTION OF PREFERRED EMBODIMENTS

Figure 1:
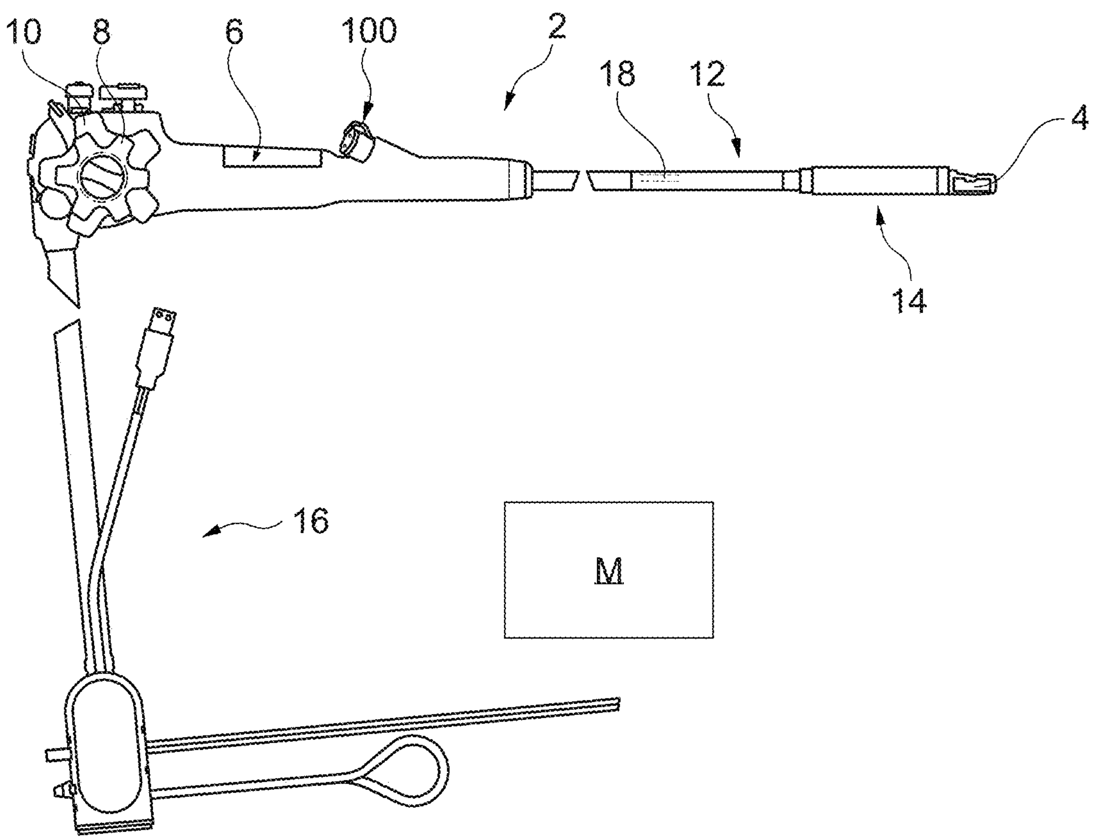
FIG. 1 is a plan view showing a system and an endoscope with a connector according to a first preferred embodiment of the present disclosure.

In FIG. 1, an endoscope 2 according to a preferred embodiment and a system with the endoscope 2 that further comprises a monitor M according to a preferred embodiment is shown. The endoscope 2 is preferably a single-use endoscope. The endoscope 2 comprises a distal tip unit 4, which is configured to be inserted into a patient's body cavity. Further, the endoscope 2 comprises a proximal endoscope handle (handle unit) 6 designed to be held by a user/ physician and being configured as a housing for accommodating operating parts (not shown) of the endoscope 2. The endoscope handle 6 comprises two handle wheels (operating units), namely a first handle wheel 8 and a second handle wheel 10, for steering the distal tip unit 4. In particular, the first handle wheel 8 and the second handle wheel 10 can both be rotated/turned by the user. The first handle wheel 8 and the second handle wheel 10 are arranged coaxially, i.e. can be rotated around a common rotational axis.

The endoscope 2 further comprises an insertion tube 12 and a bending section 14, the insertion tube 12 and the bending section 14 extending from the endoscope handle 6 to the distal tip unit 4 and thus connecting the endoscope handle 6 and the distal tip unit 4. That is to say, an insertion cord of the endoscope 2 comprises the insertion tube 12, the bending section 14 and the distal tip unit 4. Moreover, a connecting unit 16 for connecting the endoscope 2 to a supply unit is shown in FIG. 1.

The endoscope 2 further comprises an internal working channel 18, which is formed as a bendable/flexible tube (not shown in FIG. 1). The working channel 18 is provided in/inside the insertion tube 12 and the bending section 14 and extends from the endoscope handle 6 towards the distal tip unit 4. The working channel 18 is accessible at the endoscope handle 6 via a connector 100. In particular, a surgical instrument may be guided through the working channel 18 into the patient's body cavity via the connector 100. The user/physician is thus able to perform medical operations such as examinations within the patient's body cavity with the surgical instrument.

In contrast to the prior art, this connector 100 in the form of a Y-connector is (adapted to be) attachable to and detachable from the endoscope handle 6 and has a specific structure. Thereby, the endoscope 2 according to the preferred embodiment provides a coupling system that allows to attach/connect/couple the connector 100 to the endoscope handle 6 and to detach/disconnect/decouple the connector when needed. The ability to disconnect the connector is mainly relevant during assembly, e.g. if a faulty connector is mounted and should be replaced, but also for disassembly e.g. for recycling. The connector may connect to the endoscope handle with some click feature to provide a semi-permanent connection, also indicating in the assembly process that the parts are connected by audible or tactile indication. After assembly it may be advantageous to permanently fix the connector 100 to the endoscope handle 6, e.g. by gluing or ultrasonic welding. The connector 100 and its specific structure will be described in further detail in the detailed description of FIGS. 3 to 10.

In order to give an overview of the general function of the endoscope of FIG. 1, the control of the endoscope is briefly described. The distal tip unit 4 may be tilted/bent/moved by bending the bending section 14 of the endoscope 2. The endoscope 2 shown in FIG. 1 is basically a two-plane bending endoscope. This means that the distal tip unit 4 may bend in a first bending plane (e.g. in an up-and-down direction) and in a second bending plane (e.g. in a right-and-left direction). In particular, one of the handle wheels 8, 10, e.g. the first handle wheel 8, can be operated by the user to bend the distal tip unit 4 in the first bending plane and the other one of the handle wheels 8, 10, e.g. the second handle wheel 10, can be operated by the user to bend the distal tip unit 4 in the second bending plane. The first bending plane is preferably perpendicular to the second bending plane. The bending section 14 essentially has a cylindrical shape/a round/circular cross-sectional shape. At the distal tip unit 4, image capturing means such as a miniature video camera and illuminating means such as light-emitting diodes or fiber optic light guides connected to a proximal source of light may be arranged/installed, such that the patient's body cavity can be illuminated and inspected and can be viewed via the monitor M.

Figure 2:
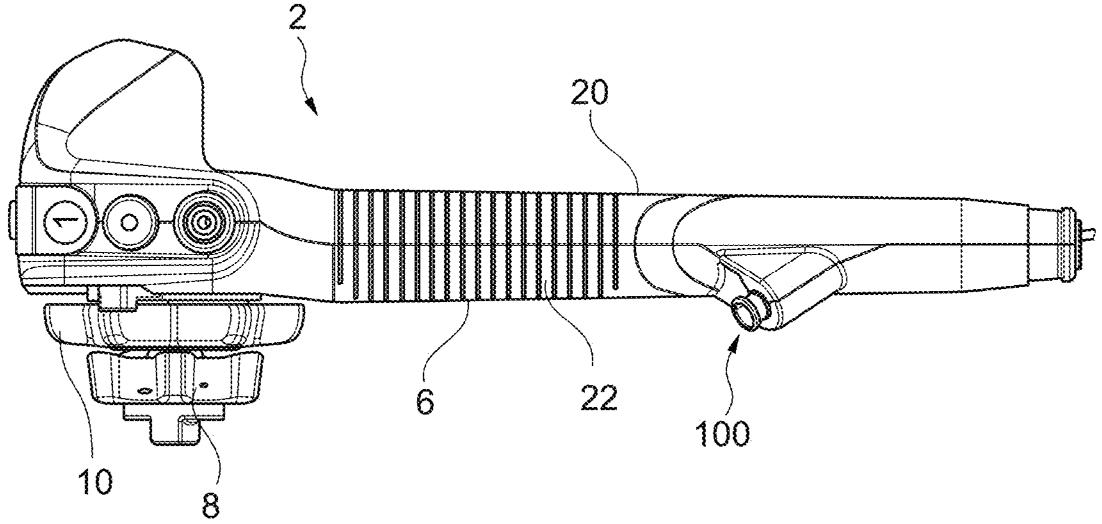
FIG. 2 is a detailed top view of an endoscope handle of an endoscope with a connector according to a second preferred embodiment.

FIG. 2 is a detailed top view of an endoscope handle 6 of an endoscope according to a second preferred embodiment. This endoscope 2 of FIG. 2 is equal to the endoscope 2 of FIG. 1 with only minor differences such as a different arrangement of valves, operating buttons and a modified distal connection to the insertion tube 12. This top view of FIG. 2 shows the handle 6 to be enclosed via two half casings along a longitudinal section, specifically a left half casing 20 and a right half casing 22. Such design of the casing of the handle 6 allows easy access to the inner structure of the endoscope handle 6, especially an easy access in order to attach and detach the connector 100 to the endoscope 2. As can be seen, the connector 100 is not aligned symmetrically with respect to a separation plane extending in the proximal and in the top direction but instead is rotated around a longitudinal axis of the working channel/of the handle 6 itself, so that the connector 100 slightly protrudes on the side of the first and second handle wheel 8, 10 respectively the right half casing 22 for improved ergonomics. Thereby the first and second handle wheel 8, 10 as well as the connector 100 is easy to reach for a user.

Figure 3:
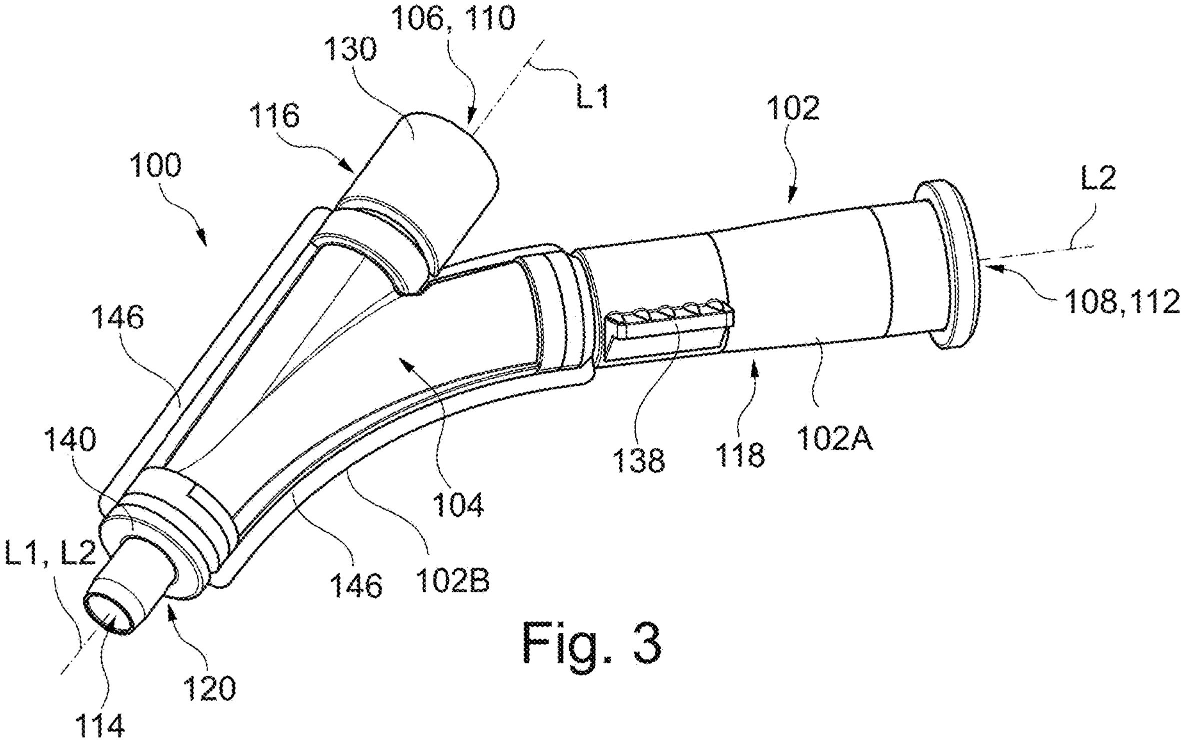
FIG. 3 is a perspective view of a two-part connector of the endoscope according to the first and second embodiment of FIGS. 1 and 2.
Figure 10:
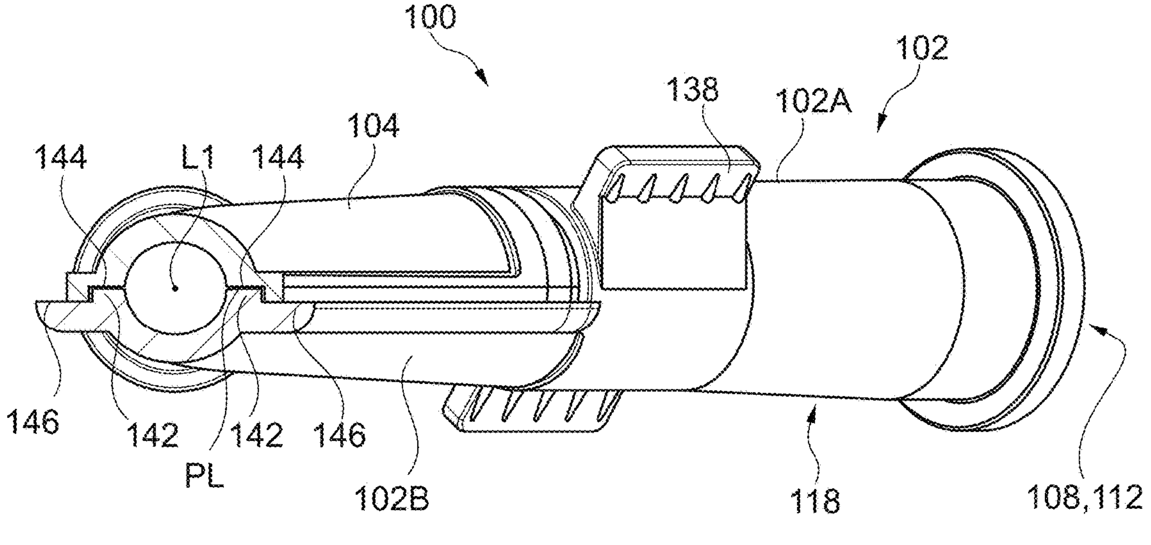
FIG. 10 is a cross-sectional view of the connector of FIG. 3 when viewed in a direction of a first longitudinal axis of a first channel of the connector.
Figure 4:
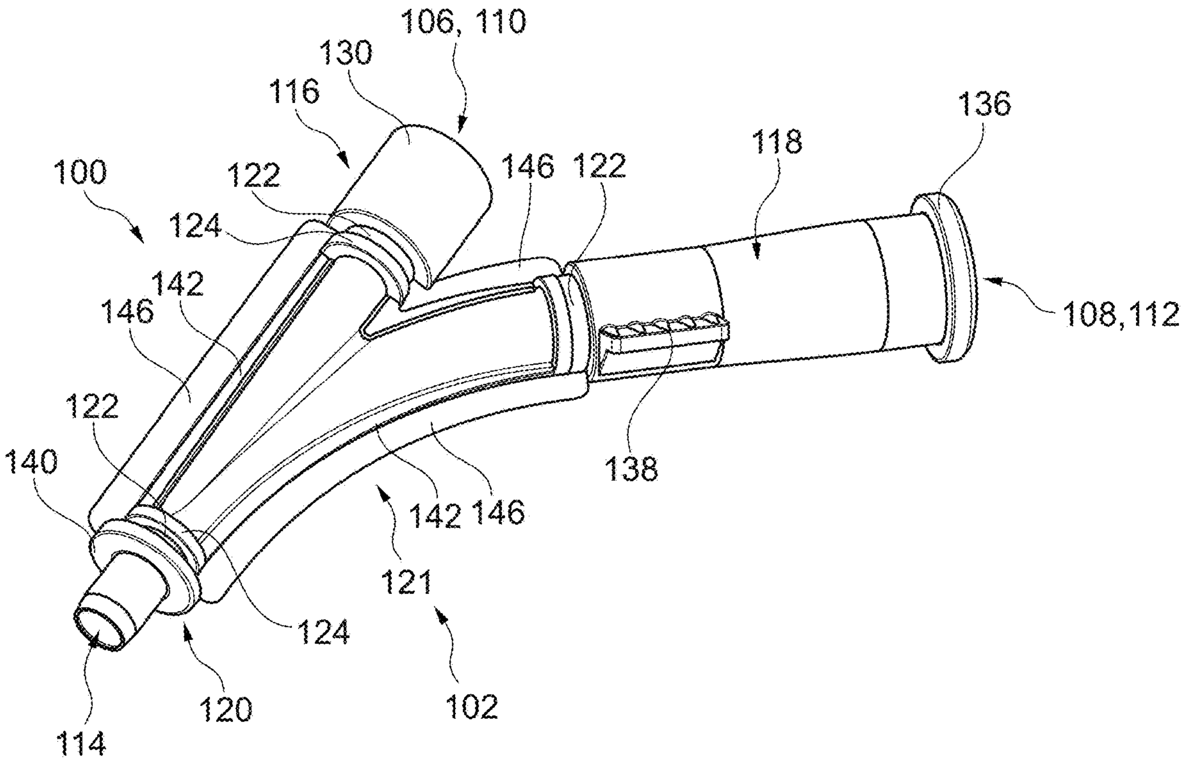
FIG. 4 is a perspective view of the two-part connector of FIG. 3 showing only a first (bottom) part of the connector.
Figure 5:
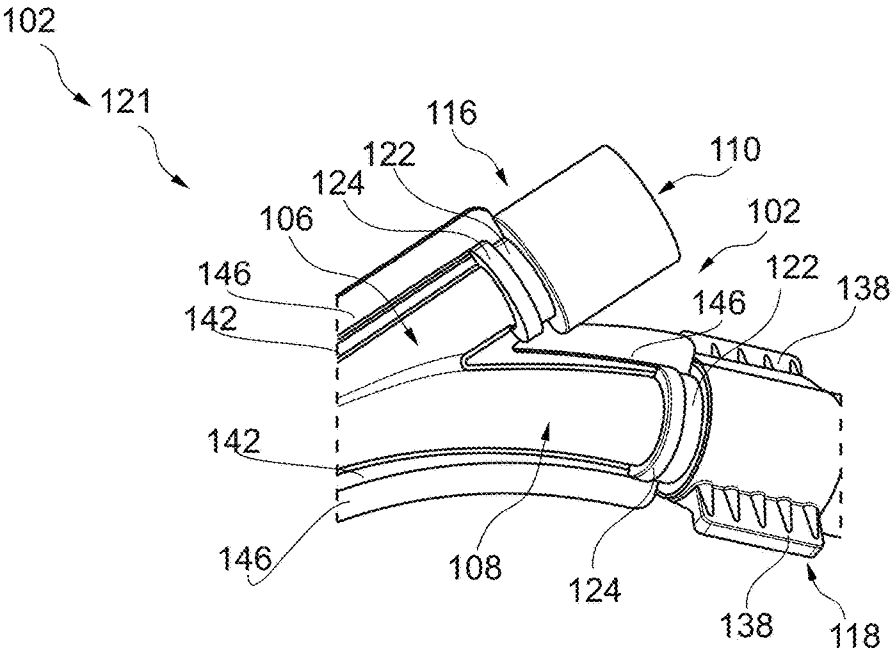
FIG. 5 is a detailed partial perspective view of the first part of FIG. 4.
Figure 6:
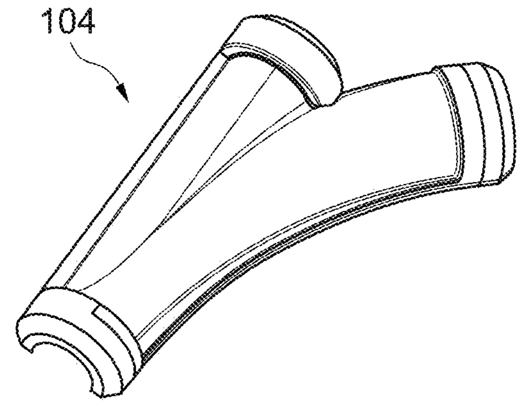
FIG. 6 is a perspective view of the two-part connector of FIG. 3 showing only the second (top) part of the connector, showing its outside structure.
Figure 7:
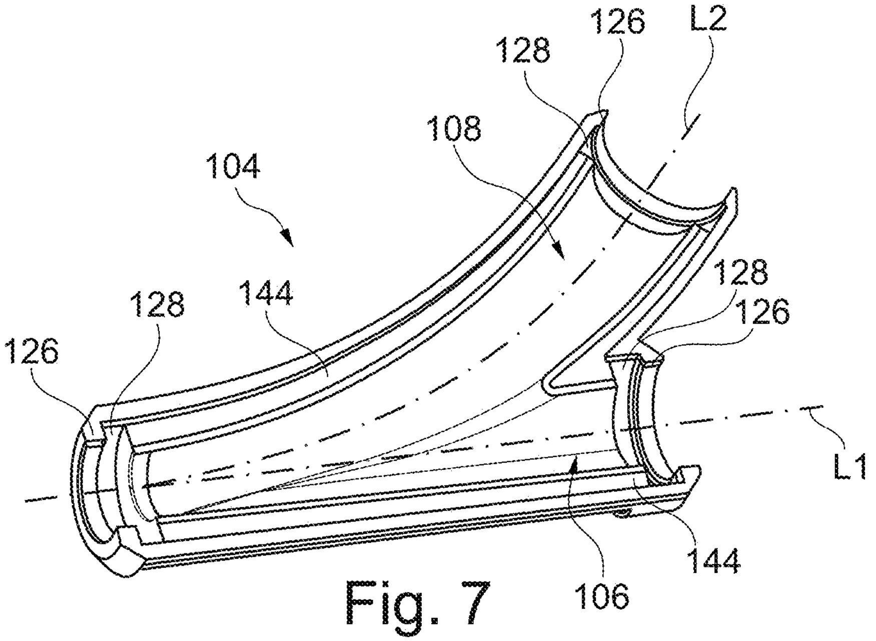
FIG. 7 is another perspective view of the second part of the connector of FIG. 6, showing the inside structure of the second part.
Figure 8:
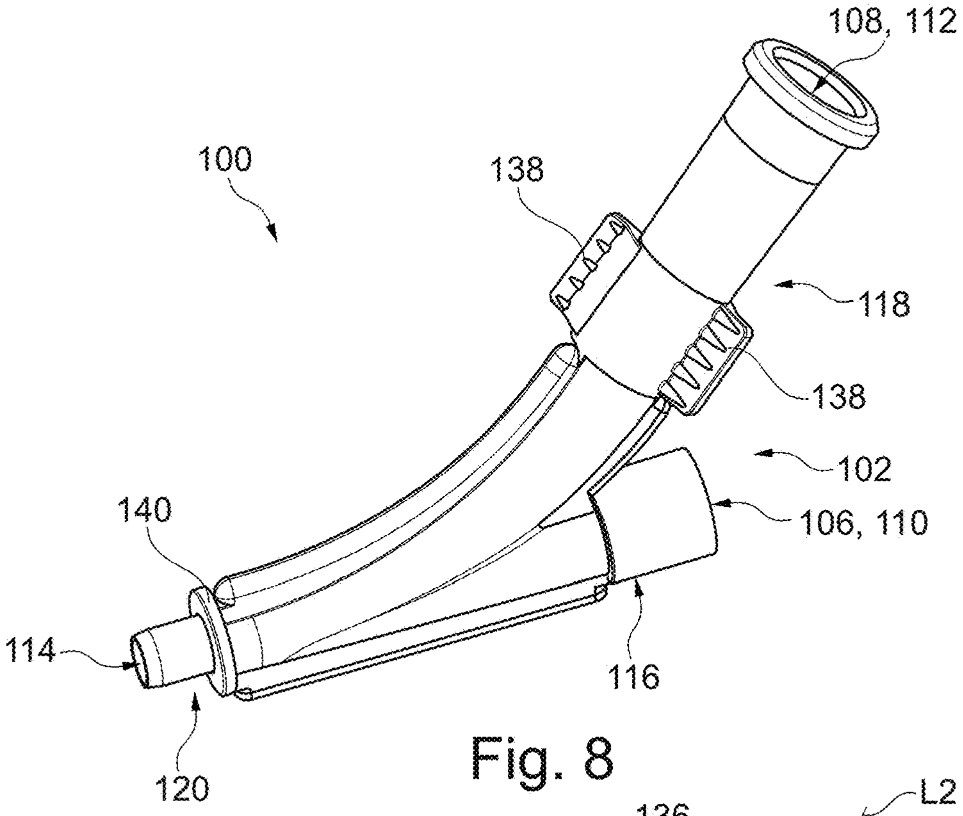
FIG. 8 is another perspective view of the two-part connector.

FIGS. 3 to 10 all show the connector 100 according to a preferred embodiment in different perspectives that is inserted into/attached to the endoscope handle 6 of the endoscope 2 of FIGS. 1 and 2. FIGS. 3, 8, 9, and 10 show the whole connector 100 with all parts, FIGS. 4 and 5 show the first part of the connector 100, FIGS. 6 and 7 show the second part of the connector 100, and FIG. 10 shows a cross-sectional view of the connector. FIG. 10 is shown on the same page with FIG. 3 to better illustrate the differences between a first part 102, having a proximal section 102A and a distal section 102B (also referred to as central portion 121 or the first part central portion 121 or the bottom half central portion 121), and a second part 104, mated with the distal section 102B in FIG. 10. The central/distal portion 102B/121 is behind the second/top part 104 in FIG. 3., but its balconies 146 are still visible.

Specifically, the connector 100 is configured as a two-piece/two-part connector 100 comprising the first part/bottom part 102 and the separate second part/top part 104 that are attached and fixed to each other. The designations top and bottom are for illustration purposes, as depicted in FIG. 10, where the top part 104 is shown above the distal section 102B of the bottom part 102. Due to the two-piece design of the connector, the bottom part and the top part each can be individually designed and adapted for an optimized manufacturing process. The particulars of FIG. 10 are described further below.

Referring to FIG. 3, connector 100 comprises a pipe shaped first channel/lumen 106 in the form of a (connector) working channel with a first circular inlet opening 110 and a pipe shaped second channel 108 in the form of a (connector) biopsy channel with a second circular inlet opening 112. The second channel 108 joins with/into the first channel 106 in a central section of the connector 100, so that the connector 100 has only one circular outlet opening 114 being in (fluid) connection with the first inlet opening 110 and the second inlet opening 112. In other words, the tubular first and second channels 106, 108 are first and second inlet branches that unite and merge together to an outlet branch with the outlet opening 114.

The first channel 106 has a straight first longitudinal axis L1 that extends from the first inlet opening 110 to the coaxial aligned outlet opening 114. The second channel 108 in turn has a second longitudinal axis L2 that has a straight section and a subsequent curved section that unites with the first longitudinal axis L1 in a common straight portion of both axis L1, L2 in the outlet opening 114. Especially the shape of the second channel 108 having a curved section makes it difficult to produce the connector 100 in one piece by moulding, e.g. injection moulding, as it would require a curved core in the moulding process, and such a curved (or rotational) core would be difficult or even impossible to remove after the moulding process, or at least require a complex and slow process, which would involve a high production cost.

When attached to the handle 6 of the endoscope 2 (see FIGS. 1 and 2), the outlet opening 114 of the connector 2 stands in fluid connection with the working channel 18 and serves as an extension of the working channel 18 extending from the outlet opening 114 through the first inlet opening 106 to a proximal section of the handle 6. In addition, the working channel 18 is in (fluid) connection with the second inlet opening 112 that serves as an access port for biopsy tools.

The bottom part 102 is configured as the bigger/larger part of the connector 100 and comprises three adapters/adapter portions/adapter sections/adapter segments 116, 118, 120 of the connector 100 for all three inlet and outlet openings 106, 108, 110 that constitute the inlet and outlet ports of the connector 100 and are adapted to be coupled to respective coupling portions of the endoscope handle 6.

A central portion of the connector 100 that is located between the adapters 116, 118, 120 is traversed by a plane that is spanned by the first longitudinal axis L1 and the second longitudinal axis L2. A top half, above the plane, constitutes the top part 104 of the connector 100. The bottom half, below the plane of this central portion, is part of the first part/the bottom part 102 of the connector 100 and structurally interconnects the adapters 116, 118, 120 with each other. In other words, the bottom part 102 comprises a bottom half central portion/section 121/102B that structurally interconnects the adapters 116, 118, 120 with each other and forms on its inner side that faces the top part 104 a gutter/a trough of the first channel 106 and of the second channel 108 that merge into each other. The top part 104 on the other hand, see especially FIG. 7, is designed complementary to the bottom half central portion 121 comprising in its inner side that faces the bottom part 102 the opposite half of the gutter/trough of the first channel 106 and of the second channel 108 that merge into each other. Thereby, when the top part 104 is attached to the bottom part 102, the adapters 116, 118, 120 together with the bottom half central portion 121 and the top half central portion (or second part central portion), in the form of the top part 104, form the first and second channels 106, 108. The bottom part 102 and the top part 104 are attached and glued together along a partition line (PL), thereby sealing the first channel 106 and second channel 108.

In yet other words, the bottom half central portion 121 and the second part 102 as the top half central portion have essentially a same basic shape of half shells that are axially symmetric to a cutting/dividing plane that is spanned by the first longitudinal axis L1 of the first channel 106 and the second longitudinal axis L2 of the second channel 108. Each half shell comprises a semi-cylinder-shaped segment along the first longitudinal axis L1 for the first channel 106 and along the second longitudinal axis L2 for the second channel 108. These two cylinder-shaped segments of each half shell merge into each other where the channels 106, 108 join each other.

Due to this specific two-part design of the bottom part 102 and the top part 104, the top part 104 has a simple structure that is mouldable without any core mould pieces whereas the bottom part 102 has a more complex structure and requires some core mould pieces, specifically three core mould pieces for each adapter 116, 118, 120 to be formed. However, because of the central portion being divided into the top half 104 and the bottom half central portion 121, even though core mould pieces are needed for the manufacturing of the bottom part 102, due to the specific structure of the bottom part 102 no rotational core mould pieces are required thus significantly improving and simplifying a production process of the bottom part 102 and thereby a production process of the connector 100 and thus of the endoscope 2. In particular, tooling costs for the manufacturing of the connector 100 can be reduced significantly.

In particular, both the bottom part 102 and the top part 104 are made of mouldable plastic, preferably thermoplastic and/or thermosetting polymers, that are simple and cost effective mouldable. Further preferred, the material of the connector 100 is a biocompatible material.

Also shown in FIG. 3 are a first sleeve 130 of the first adapter 116, forming the first inlet opening 110, two wings 138 of the second adapter 118, a coaxial ring-shaped disc 140 of the outlet adapter 120, and a pair of balconies 146 of the first part 102. These elements are described below.

Referring now to FIG. 4, each of the three adapters 116, 118, 120 comprises at its part/side facing away from its respective openings 110, 112, 114 a semi-circular groove 122 in a circumferential direction with respect to the respective first and second longitudinal axis L1, L2 at the radial outer surface of each adapter 116, 118, 120. In other words, the groove 122 extends perpendicular to the respective longitudinal axis L1, L2 (at this position). Besides the groove 122 and along with it, an adjacent, coaxially aligned semi-circular projection/arch 124 is formed at the radial outer surface that is provided opposite to the respective opening 110, 112, 114 seen in the axial direction. This structure serves for formfitting with the top part 104 (see FIG. 7). Specifically the semi-circular grooves 122 of each adapter 116, 118, 120 form-fits with corresponding semi-circular projections 126 at the front of the respective branch of the top part 104 and the projections 124 form-fits with corresponding (adjacent) semi-circular grooves 128 of the top part 104, thereby as well sealing the first and second fluid channels 106, 108 at its end sides.

In order to further improve sealing capabilities, the bottom part 102 comprises in the bottom half central portion 121 on both sides of the first and second channels 106, 108 longitudinal barrier bars 142 that extend parallel to the longitudinal axis L1, L2 and serve as partition walls with respect to the channels 106, 108. The top part 104 on the other hand comprises complementary longitudinal recesses 144 (shown in FIG. 7) that form-fit with the longitudinal barrier bars 142 and seal the channels 106, 108 towards the side. In a virtual section perpendicular to the longitudinal axis L1, L2 (the section of) the barrier bar 142 and its neighbouring surrounding is similar to a L-shape that interacts with the recess and its neighbouring surrounding that as well is forming kind of a L-shape. Both L-shapes are facing each other with the short side of the L form abutting the long side of the L, similar to two snap-noses. Thereby, a form locking as well as a sealing is achieved (see in particular FIG. 10). This construction is advantageous when the two parts are glued together, as the barrier bars 142 and recesses 144 prevent or restrict the glue from flowing into the channels.

Figure 9:
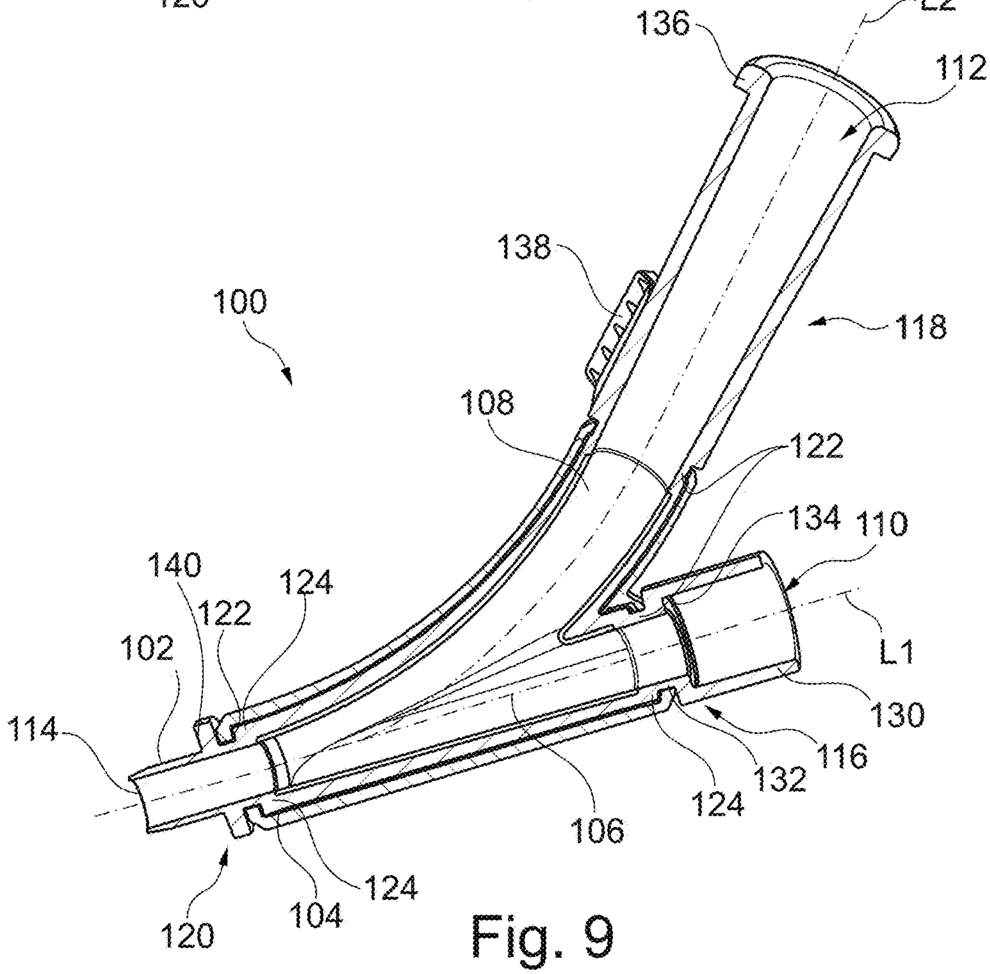
FIG. 9 is a longitudinal section view of the connector of FIG. 8.

Referring in particular to FIG. 9, the three adapters/adapter portions 116, 118, 120 of the first part 102 have a special structural configuration for on the one hand providing a specific coupling (adapter) to the endoscope handle 6 and on the other hand to be easily moulded without any rotational core mould pieces. Each adapter 116, 118, 120 is described in the following.

The first adapter/adapter portion 116 comprises a first sleeve 130 and an adjacent coaxial second sleeve 132. The first sleeve 130 is forming the first inlet opening 110 having a first inner diameter and the second sleeve 132 has a second inner diameter that is smaller than the first inner diameter. Thereby a circumferential stop step 134 in the axial direction is formed at a radial inner side.

The second adapter/adapter portion 118 is in the form of a sleeve having a coaxial ring-shaped front flange 136 at its radial outer surface at its free end that means at the end side/axial position of the second inlet opening. The second adapter 118 further comprises two wings 138 on opposite radial outer sides of the sleeve, each wing 138 being in the form of a flat plate extending from the radial outer sleeve surface in the radial outward direction and in the axial direction of the sleeve. The two wings 138 serves as a protruding structure that is used for aligning and together with complementary snap-in structures (not shown) of the endoscope handle 6 for fixation of the connector 100 inside the two halves 20, 22 (see FIG. 2).

The third, or outlet, adapter/adapter portion 120 is in the form of a sleeve having a coaxial ring-shaped disc 140 at its radial outer surface distant to the outlet opening 114. The disc 140 is formed perpendicular to the longitudinal axis L1 and L2 and is formed to abut against the attached top part 104. The front part of the outlet adapter 120 is in the form of a connecting nozzle with a slight circumferential chamfer on its front radial outer surface extending about 25% of the length of the outlet adapter sleeve along the longitudinal axis L1.

Referring in particular to FIG. 10, bottom part 102 of the connector 100 comprises at its bottom half central portion 121 on both sides of the first channel 106 and as well as of the second channel 108 balconies 146 in the form of bar stripes/protrusions along the partition lines, each balcony 146 serving as an extended platform for supporting an assembly and a glue to flow into a gap between the first part 102 and the top part 104 (see assembled connector in FIG. 3). The balconies 146 ease an assembly in that a glue pen (not shown) can rest on the balcony and glue flows into the gap between the two parts 102, 104, also by capillary effect.

Figure 11:
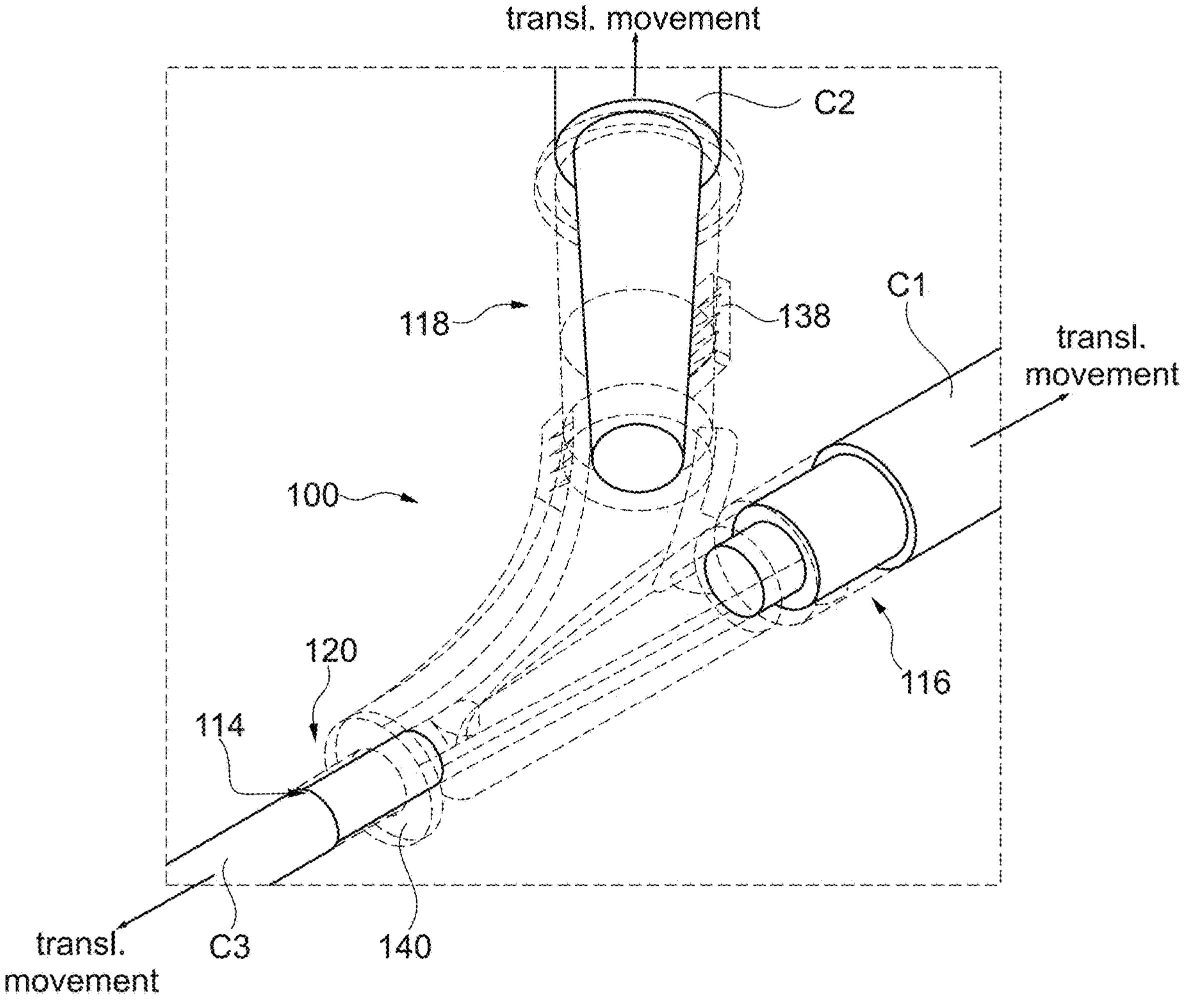
FIG. 11 is a schematic, partially transparent isometric view of the first part of the connector that is produced according to a method according to a preferred embodiment.

In the following, a method for producing an endoscope according to a preferred embodiment of the present disclosure is described. In particular, FIG. 11 schematically shows how the bottom part 102 of the connector 100 is produced according to the preferred method for producing an endoscope. In specific, the bottom part 102 is produced by injection moulding using only straight moulding cores/straight core mould pieces C1, C2, C3. All three straight moulding cores C1, C2 and C3 have a rotationally symmetric shape along a straight central axis and all are arranged in an injection moulding device (not shown).

The first straight moulding core C1 has a shape of three coaxially aligned cylinders with three different diameters, the diameters of the cylinders decreasing towards the centre respectively the bottom half central portion 121. This specific cylindrical shape is complementary to the radial inner surface of its respective first adapter portion 116 with its stop 134. The second straight moulding core C2 has a shape of a conical frustum attached to a cylindrical base with a larger diameter (thereby forming a cylindrical step along the circumference), the diameter of the conical frustum continuously decreasing towards the bottom half central portion 121. The third straight moulding core C3 has a shape of two coaxially aligned cylinders with two different diameters, the diameters of the cylinders again decreasing towards the bottom half central portion 121. Hereby, all three straight moulding cores C1, C2 and C3 can be removed in a simple translational movement in an outward direction of the respective adapters 116, 118, 120 after moulding, since the diameters are decreasing and there is no recess in the direction of its respective central axis. In other words, they can be withdrawn in the direction of the first longitudinal axis L1 and the second longitudinal axis L2 (directions at the locations of the respective adapters 116, 118, 120). Such method of moulding the bottom part 102 is rapid, effective and reduces tooling costs.

Figure 12:
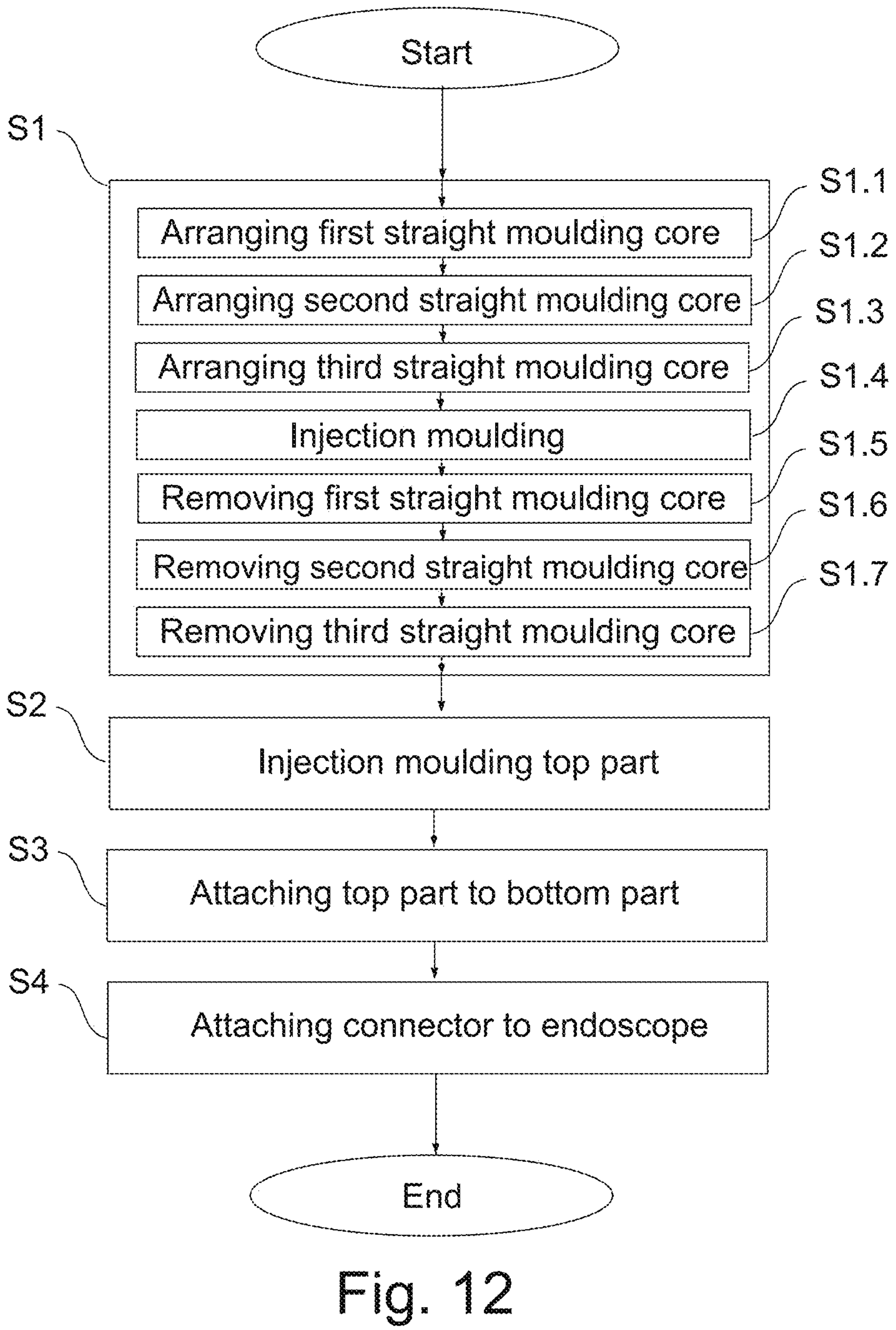
FIG. 12 is a flow chart of a method for producing an endoscope according to the preferred embodiment.

FIG. 12 shows a flow chart of a preferred method of the present disclosure for producing the endoscope 2 with the multi-piece connector 100 of the present disclosure. In general, in a first step S1, the bottom part 102 of the multi-piece connector 100 is moulded. In a second step S2, the top part 104 of the multi-piece connector 100 is moulded. Alternatively, the top part 104 may by moulded in a first step and the bottom part may be moulded in a second step or both parts 102, 104 may be moulded parallel at the same time. In other words, the order of moulding S1 the bottom part 102 and moulding S2 the top part 104 is not relevant. Thereafter, in a third step S3, the second part 104 is attached to the first part 102 thus assembling the connector 100, and both parts 102, 104 are glued together along the partition line, thereby permanently fixing the bottom part 102 to the top part 104. Finally, in a fourth step S4, the assembled multi-piece connector 100 is attached to the endoscope 2 and is glued and/or laser welded to the endoscope for permanent fixation.

In the following, the steps S1 and S2 of moulding of the bottom part 102 and the top part 104 are described in more detail.

In specific, in the second step S2, the top part 104 is moulded by injection moulding and due to its simple structure requires no core mould pieces/moulding cores during moulding. However, the bottom part 102 is more complex but due to the method according to the present disclosure can be moulded without any rotational core mould pieces. Specifically, the step S1 of moulding the first part 102 comprises (sub)steps of S1.1 arranging a first straight moulding core C1, S1.2 arranging a second straight moulding core C2 and S1.3 arranging a third straight moulding core C3 in the injection moulding device. In the step S1.4 of injection moulding the bottom part 102 of the connector 100, the first straight moulding core C1 serves/is used to form the first adapter portion 116 with the first inlet opening 110 of the first channel 106 of the connector 100, the second straight moulding core C2 serves to form the second adapter portion 118 with the second inlet opening 112 of the second channel 108 of the connector 100 and the third straight moulding core C3 serves to form the outlet adapter portion 120 with the outlet opening 114 of the connector 100. After injection moulding in step S1.4, in step S1.5 the first straight moulding core C1 is removed by moving/retracting the first moulding core C1 along the first longitudinal axis L1 out of the moulded bottom part 102. Further, in step S1.6 the second straight moulding core C2 is removed and in step S1.7 the third straight moulding core C3 is removed, each straight moulding core C1, C2, C3 withdrawn by a translational (retraction) movement.

List of reference signs:

2 endoscope
4 distal tip unit
6 endoscope handle
8 first handle wheel
10 second handle wheel
12 insertion tube
14 bending section
16 connecting unit
18 working channel
20 First casing
22 second casing
100 connector
102 First part/bottom part
104 second part/top part
106 first channel/working channel
108 second channel/biopsy channel
110 first inlet opening
112 second inlet opening
114 outlet opening
116 first adapter (portion)
118 second adapter (portion)
120 outlet adapter (portion)
121 bottom half central portion
122 groove
124 projection
126 corresponding projection
128 corresponding groove
130 first sleeve
132 second sleeve
134 stop
136 front flange
138 wing
140 ring disc/flange
142 barrier bar
144 recess
146 balcony
S1 step moulding bottom part
S1.1 step arranging first straight moulding core
S1.2 step arranging second straight moulding core
S1.3 step arranging third straight moulding core
S1.4 step injection moulding
S1.5 step removing first straight moulding core
S1.6 step removing second straight moulding core
S1.7 step removing third straight moulding core
S2 step moulding top part
S3 step attaching top part to bottom part
S4 step attaching connector to endoscope
L1 longitudinal axis first channel
L2 longitudinal axis second channel
M Monitor

The invention claimed is:

1. An endoscope comprising:
a distal tip;
a handle;
an insertion tube and a bending section, the insertion tube and the bending section connecting the handle and the distal tip;
a working channel provided in the insertion tube and the bending section and extending from the handle towards the distal tip inside the insertion tube and the bending section;
a connector positioned in the handle and including a first part and a second part formed separately from and attached to the first part, the connector having a central portion, a first inlet opening, a second inlet opening, and an outlet opening, a first channel extending from the first inlet opening to the outlet opening, and a second channel extending from the second inlet opening to the outlet opening, the outlet opening being in connection with the working channel, the first channel and the second channel merging at the central portion,
the first part comprising;
a second adapter portion and a first part central portion, the second adapter portion defining the second inlet opening and a proximal portion of the second channel, and the second part and the first part central portion forming a distal portion of the second channel, and
a third adapter portion forming the outlet opening, the third adapter portion being in the form of a sleeve having an outer surface and a ring disc extending radially outwardly from the outer surface, the ring disk being located proximally of the outlet opening
wherein the first part central portion and the second part are bonded together along at least one partition line to seal the first channel and the second channel.

2. The endoscope of claim 1, wherein the first part also comprises a first adapter portion forming the first inlet opening of the first channel.

3. The endoscope of claim 1, wherein the first part and/or the second part comprises at least one balcony in form of a protrusion or a bar extending at least partially along the at least one partition line.

4. The endoscope of claim 3, wherein the first part and the second part are bonded with glue, the at least one balcony allowing the glue to flow into a gap between the first part and the second part.

5. The endoscope of claim 3, wherein the at least one partition line comprises two partition lines, wherein the at least one balcony comprises two balconies extending on opposite sides of the first part and/or the second part, and wherein the two balconies serve to support the connector during assembly while bonding the first part and the second part together.

6. The endoscope of claim 1, wherein the first part also comprises a first adapter portion forming the first inlet opening of the first channel, and wherein the first part central portion interconnects the first adapter portion, the second adapter portion, and the third adapter portion.

7. The endoscope of claim 6, wherein the second part is in the form of a second part central portion configured to cover the first part central portion when attached to the first part.

8. The endoscope of claim 6, wherein the first part central portion and the second part have mirror-image inner surfaces.

9. The endoscope of claim 6, wherein the first part comprises at least one partly circumferential groove, and wherein the second part comprises at least one partly circumferential projection received by the at least one partly circumferential groove.

10. The endoscope of claim 9, wherein the at least one partly circumferential groove is comprised by the first adapter portion and/or the second adapter portion and/or the third adapter portion, at a side thereof facing away from the respective inlet or outlet opening.

11. The endoscope of claim 1, wherein the first part also comprises a first adapter portion forming the first inlet opening of the first channel, wherein the first adapter portion comprises a first sleeve and a second sleeve adjacent to and coaxial with the first sleeve, the first sleeve forming the first inlet opening, the first inlet opening having a first inner diameter, and wherein the second sleeve has a second inner diameter that is smaller than the first inner diameter and forms a stop step in an axial direction at a radial inner side of the first adapter portion.

12. The endoscope of claim 1, wherein the second adapter portion is in the form of a sleeve having a free end and a flange at the free end, the flange having a radial outer surface.

13. The endoscope of claim 1, wherein the second adapter portion is in the form of a sleeve having a free end, an outer surface, and a flange at the free end, the flange having a radial outer surface, wherein the second adapter portion further comprises two wings on a side opposite the free end, each of the two wings being in the form of a flat plate extending radially outwardly from the outer surface and in an axial direction of the second adapter portion.

14. The endoscope of claim 1, wherein the ring disc abuts against the second part.

15. The endoscope of claim 1, wherein the first channel comprises a first axis that is straight, the first inlet opening being coaxial with the outlet opening.

16. The endoscope of claim 15, wherein the second channel comprises a second axis passing through a center of the second inlet opening and intersecting the first axis at an angle between 30° and 50°.

17. A system comprising:

the endoscope of claim 1; and a monitor.

* * * * *